United States Patent [19]
Songer

[11] Patent Number: 6,156,035
[45] Date of Patent: Dec. 5, 2000

[54] ELECTROCAUTERY METHOD AND APPARATUS

[75] Inventor: Matthew N. Songer, Marquette, Mich.

[73] Assignee: Pioneer Laboratories, Inc., Marquette, Mich.

[21] Appl. No.: 09/192,787

[22] Filed: Nov. 16, 1998

Related U.S. Application Data

[62] Division of application No. 08/784,735, Jan. 13, 1997, Pat. No. 5,876,400.

[51] Int. Cl.⁷ .................................................. A61B 18/18
[52] U.S. Cl. .............................. 606/45; 606/41; 604/21
[58] Field of Search ................................ 606/41, 42, 45, 606/46, 48–50; 604/21, 22, 49, 51

[56] References Cited

U.S. PATENT DOCUMENTS

| | | |
|---|---|---|
| 3,595,239 | 7/1971 | Petersen . |
| 4,592,372 | 6/1986 | Beranek ................................... 607/122 |
| 4,832,048 | 5/1989 | Cohen ........................................ 606/41 |
| 4,976,684 | 12/1990 | Broadnax, Jr. . |
| 5,197,963 | 3/1993 | Parins . |
| 5,221,281 | 6/1993 | Klicek . |
| 5,242,441 | 9/1993 | Avitall ........................................ 606/41 |
| 5,300,070 | 4/1994 | Gentelia et al. . |
| 5,348,554 | 9/1994 | Imran et al. ............................... 606/41 |
| 5,383,876 | 1/1995 | Nardella . |
| 5,417,687 | 5/1995 | Nardella et al. . |
| 5,429,636 | 7/1995 | Shikhman et al. . |
| 5,599,348 | 2/1997 | Gentelia et al. . |
| 5,605,539 | 2/1997 | Buelna et al. . |
| 5,643,257 | 7/1997 | Cohen et al. .............................. 606/48 |

OTHER PUBLICATIONS

Article by Michael F. Gleeson, MD, FACS entitled: A Blunt–Tipped, Electronically–Controlled, Laparoscopic Trocar System 5 pages, presented in Oct. 1994 at the annual meeting of the American College of Surgeons of Chicago, Illinois.

Brochure of ConMed Surgical Systems entitled: "Select One Minimal Access Surgery System", 6 pages.

*Primary Examiner*—Michael Peffley
*Attorney, Agent, or Firm*—Garrettson Ellis Seyfarth Shaw

[57] ABSTRACT

An electrocautery probe for penetrating through tissue. The probe comprises a tissue-compatible, flexible sleeve; an exposed electrode carried at one end of the sleeve; a wire connected at one end to the electrode and extending through the sleeve; and an electrical connector attached to the other end of the wire. The connector is suitable for attachment to a source of electrocautery power. The wire is separate from the sleeve, to be removable by pulling from the sleeve when the electrode is cut away or otherwise removed from the sleeve. Thus, the probe can penetrate tissue by electrocautery action to form a tissue tunnel, and the electrode and wire can then be removed, leaving at least a portion of the sleeve in the tissue tunnel to serve as a drainage catheter.

17 Claims, 1 Drawing Sheet

ELECTROCAUTERY METHOD AND APPARATUS

CROSS REFERENCE TO RELATED APPLICATION

This application is a division of Songer application Ser. No. 08/784,735, filed Jan. 13, 1997 now U.S. Pat. No. 5,876,400.

BACKGROUND OF THE INVENTION

Electrocautery systems are used as a substitute for a mechanical, sharp trocar for the purpose of forming tunnels through tissue for surgery for the emplacement of drainage tubes and the like.

For example, the TroGard Electronic Trocar system of ConMed Surgical Systems of Utica, N.Y. comprises such a system. Such an electronic trocar has a blunt tip, and can be advanced with electrocautery action to create a small tunnel through the tissue inwardly from the skin, to dilate the tissue to a desired size for instrument access to the interior. Typically an obturator is inserted into the tunnel.

A significant advantage of such an electronic trocar is that, unlike a mechanical trocar, its tip cannot penetrate and injure the finger of the surgeon as it is being used. The rubber gloves that the surgeon is wearing provide substantial protection against electronic burning of his fingers during the process if his finger inadvertently touches the electronic trocar tip. Also, a surgeon can be protected against accidental puncture wounds by an electronic trocar. The passing of sharp drain trocars are particularly dangerous risks for puncture injuries to the surgeon's hands.

By this invention, a drainage tube may be simultaneously implanted as the electronic trocar is advanced, for a great savings of time and effort expended during surgical procedures.

DESCRIPTION OF THE INVENTION

By this invention, a wound drain may be installed in a patient by the method which comprises the following steps. One inserts, by electrocautery action and effect, an electrocautery probe through tissue between the inside cavity of a wound and the skin of a patient. Typically, the wound can be a surgical incision of the type which requires drainage for a few days after the surgery. The electrocautery probe which is used comprises a wire, a sleeve surrounding the wire, and an exposed electrode which is connected to the wire and positioned at a forward end of the sleeve. The wire is also connected at a rear end to a source of electrocautery energy, typically a conventional electrocautery power unit.

After insertion of the electrocautery probe to penetrate a desired distance, and typically forming a tunnel between the inside cavity of the wound and skin and also extending through the skin, the electrode is removed from the sleeve, and the wire is pulled out of the sleeve, typically disconnecting it first from the source of energy. Thus, the sleeve remains positioned in the tissue tunnel between the inside cavity of the wound and the skin of the patient to serve as a wound drain.

Typically, the electrocautery probe may be inserted through the tissue from the wound area, being advanced toward and through the skin. By so doing, the outward motion of the probe relative to the skin reduces the possibility that skin bacteria can be drawn into the tunnel or the wound.

The wire, which may be a single or multiple wire or cable, and the electrode, which may be a monopolar or bipolar electrode, may be surrounded by a conventional, tubular insulating layer for the wire within the sleeve. The insulating layer is in that circumstance slidably removable from the sleeve along with the wire.

It is also preferred for the probe to have a blunt forward end, so that it cannot effectively penetrate the skin except through electrocautery action. Thus the surgeon is protected from accidental stabbing of his or her fingers as the probe emerges from the skin at the end of tunnel formation through the tissue. The probe preferably is advanced through intact tissue which is free of prior cutting as by a trocar or the like in its path between the inside cavity of the wound and the skin of the patient, with the advancement being primarily by electrocautery action rather than mechanical cutting.

It is also generally preferred, after the tunnel has been formed and the electrode has been positioned outside of the skin, to cut or otherwise remove the electrode away from the wire, and to pull the wire out of the sleeve retrograde through the wound.

Thus, an electrocautery probe in accordance with this invention for penetrating through tissue may comprise a tissue-compatible, flexible sleeve made for example of silicone rubber, polyethylene, or the like. An exposed electrode is carried at one end of the sleeve, with a wire connected at one end to the electrode, the wire extending through the sleeve, and an electrical connector being attached to the other end of the wire. The connector is typically suitable for attachment to a conventional source of electrocautery power.

The wire is separate from the sleeve, so that it is removable by pulling from the sleeve when the electrode is cut away or otherwise removed from the sleeve. Thus, the probe can penetrate tissue by electrocautery action to form a tissue tunnel, and the electrode and wire can then be removed, leaving the sleeve in the tissue tunnel to serve as a drainage catheter. The sleeve may then be cut to a desired length. As previously stated, it is preferred for the electrode end of the sleeve to be blunt so as to be essentially incapable of penetrating tissue without electrocautery action.

The method and apparatus of this invention may be used in any desired surgical procedure, and are particularly useful in orthopaedic use, particularly in the areas that are difficult to pass a drain, for example in the area of the spinal, hip, or pelvic regions. The system is also usable elsewhere, for example in abdominal use, chest or breast surgery, and the like.

Typically, the sleeve is attached to the electrode by bonding or the like so that is cannot be displaced along the probe until the electrode has been transversely cut or otherwise removed away from the rest of the probe. The insulating layer surrounding the wire may be of a desired stiffness to provide an appropriate, overall stiffness to the probe for purpose of advancing through tissue in a precise, controlled manner. At the same time, the separable insulating sleeve can be soft and of the desired physical characteristics of conventional wound drain tubing. The wire may also be thick near the electrode to provide a desired stiffness, while yet permitting bending.

DESCRIPTION OF SPECIFIC EMBODIMENTS

Figure 1:
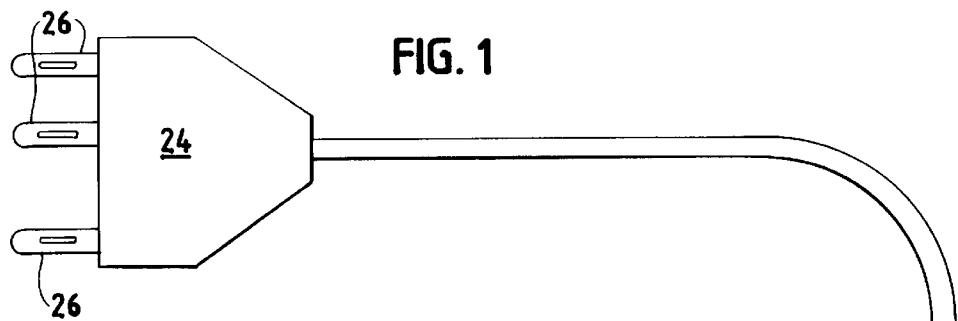
FIG. 1 is a plan view of the electrocautery probe of this invention.
Figure 2:
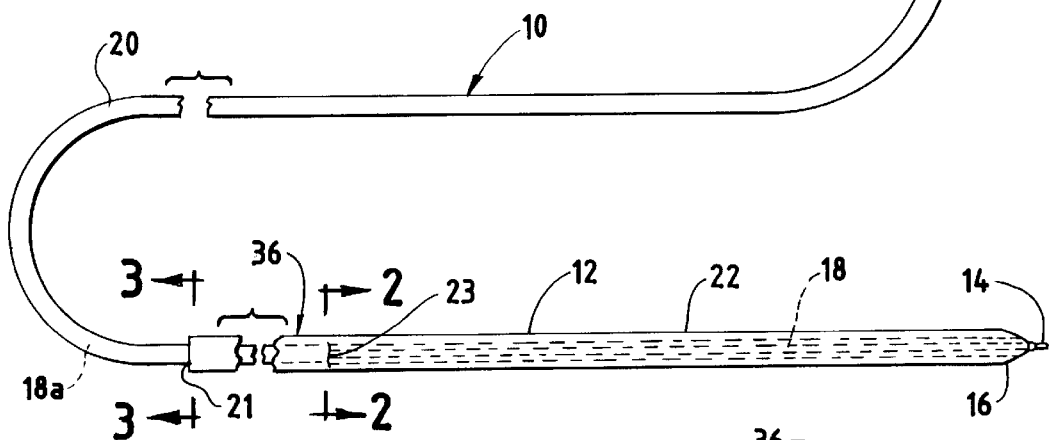
FIG. 2 is an enlarged, sectional view taken along line 2—2 of FIG. 1.
Figure 2:
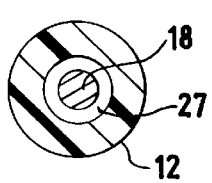

Referring to FIGS. 1 and 2, electrocautery probe 10 is shown, comprising a tissue compatible silicone rubber sleeve 12 which is proportioned to be of the diameter of a desirable surgical drainage tube, and being soft and of physical properties desirable for such drainage tubing.

An electrode 14 exposed to the exterior, is carried at one end of silicone rubber sleeve 12 with the forward or distal end 16 of sleeve 12 being secured to electrode 14 by an adhesive, a wedge-press fit, or the like, so that sleeve 12 is retained in its desired position as shown adjacent electrode 14.

Figure 3:
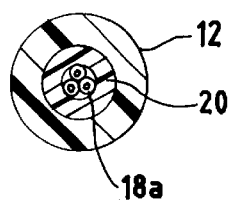
FIG. 3 is an enlarged, sectional view taken along line 3—3 of FIG. 1.

Electrode 14 is connected to a wire 18, which is connected at its other end to wire 18a. Wire 18 may be a single, thick wire, extending for the first few inches of the probe length. In this embodiment, electrode 14 is monopolar and conventionally suitable for use in electrocautery. Wire 18a comprises a group of thinner wires and connects to wire 18, being surrounded by a tubular insulating layer 20. Wire 18 may or may not be surrounded by layer 20, and may be of greater wire diameter than wire 18a, as shown in FIGS. 2 and 3. Wire 18 may comprise a thick, malleable wire, which not only provides electrical communication between wire 18a and electrode 14, but may be thick enough to be bent and to hold its shape, so that the surgeon may bend the forward portion 22 of probe 10 to a desired shape during use. As shown in FIG. 2, wire 18 fits loosely in sleeve 12 with extra space 27 instead of an insulating layer.

About five inches proximal from the electrode tip 14, the thick wire portion 18 ends (at point 23), and connects by soldering or clamping with the group of smaller, flexible wires 18a, which extend proximally (rearwardly) within insulating sheath 20, providing an electrical conductor section of electrocautery probe 10 which is more flexible than portion 22.

About 36 inches proximal from exposed electrode tip 14, silicone rubber sleeve 12 terminates at point 21, while two or three strand conductor 18a, surrounded by insulating layer 20, extends rearwardly further to terminate in a conventional electrical connector 24. Electrical connector 24 carries three prongs, each of which could connect to a different one of three wires in multiple wire 18a, especially for use with a bipolar electrode. One of prongs 26 may connect to ground; one of prongs 26 may connect to a first voltage source in a conventional electrocautery machine for coagulation; and the third of the prongs may connect to a second voltage source which is suitable for imposing a cutting voltage on electrode 14.

Alternatively, optimally a single prong 26 may directly connect to a conventional electrocautery machine through an adapter without the conventional electrical connector 24.

However, in this embodiment, one or more of the wires of conductor 18a may connect to one single prong 26, which imposes a cutting voltage on monopolar electrode 14, and one or more wires 1a connects to ground through another prong 26. The third prong may be a dummy prong, present to facilitate connection with a conventional connector receptacle.

Many of the components disclosed, excluding silicone sleeve 12 and the distal tip design, can be found in prior art electrocautery probes.

Figure 4:
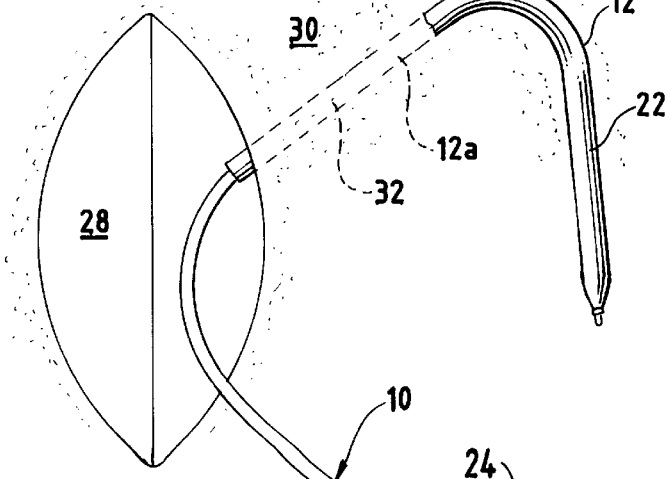
FIG. 4 is an enlarged, plan view of a surgical wound in a patient as shown during an intermediate stage of the surgery, and further showing how the electrocautery probe may be advanced through tissue to form a tunnel that extends between the wound and the skin, with the probe penetrating through the skin.

Referring to FIG. 4, the use of the electrocautery probe of this invention is illustrated.

A surgical wound 28 in the skin 30 of a patient is shown. Prior to sewing up the wound, surgical drains often need to be emplaced. To accomplish this, the electrocautery probe 10 of this invention is used. Probe 10 is advanced from the inside cavity of wound 28 through intact tissue of the patient under the skin 30, to exit the skin, as shown. The front probe portion may be manually curved as desired using thick wire 18. The probe is advanced until electrode 14 projects outwardly from the skin.

Silicone sleeve 12 advances through the entire length of the surgical tunnel 32 that is formed by this process. Power from power source 29 provides the electrocautery action that permits the advancement of electrode 14 through the tissue and out of the skin.

Then, electrode 14 may be transversely cut away or otherwise removed. Typically it may be transversely cut through somewhere along the length of silicone sleeve 12, preferably proximal of thick wire 18, such as at arrow 36 (FIGS. 1 and 4), and removed along with thick wire 18. Then, the remaining wire 18a, and its insulation 20 may be withdrawn retrograde out of sleeve 12 through wound 28, leaving behind a simple, silicone, tubular wound drain 12a which formerly surrounded the wire and insulation. Silicone tube 12a may be cut to its desired length, and wound 28 may be sutured, thus providing an installed wound drain, eliminating the need for several intermediate steps of the prior art installation of wound drains.

The above has been offered for illustrative purposes only, and is not intended to limit the scope of the invention of this application, which is as defined in the claims below.

That which is claimed:

1. An electrocautery probe for penetrating through tissue, which comprises:

a tissue-compatible, flexible sleeve; an exposed electrode carried at one end of and immovably connected to said sleeve; a wire connected at one end to said electrode and extending through said sleeve, and an electrical connecter attached to an end of said wire opposed to said one end, said connector being suitable for attachment to a source of electrocautery power, said wire being substantially separate from said sleeve to be removable by pulling from said sleeve when said electrode is cut away or otherwise removed from the sleeve, whereby said probe can penetrate tissue by electrocautery action to form a tissue tunnel, and said electrode and wire can then be removed, leaving the sleeve in the tissue tunnel to serve as a drainage catheter, said wire comprising a distal, relatively thick wire portion adjacent said electrode, said thick wire portion being of a thickness to be manually bendable while tending to retain a shape to which it is bent; and a proximal, relatively thin wire portion having more flexibility than said thick wire portion, said wire portions being electrically connected together.

2. The probe of claim 1 in which said sleeve comprises silicone rubber.

3. The probe of claim 1 in which said one end of the probe is blunt so as to be essentially incapable of penetrating tissue without electrocautery action.

4. The probe of claim 1 in which at least a portion of said wire remote from said electrode is surrounded by a tubular insulating layer, said insulating layer being slidably removable from the sleeve along with said wire.

5. The probe of claim 1 in which said flexible sleeve fully encloses said thick wire portion and extends proximally from said thick wire portion along said thin wire portion.

6. The probe of claim 5 in which said thin wire portion has an insulation layer, while said thick wire portion is free of added insulation, above and beyond said sleeve.

7. The electrocautery probe of claim 1 in which said wire is free of insulation adjacent to said one end apart from any insulation provided by said sleeve, and said wire adjacent to said one end fits loosely in said sleeve.

8. The electrocautery probe of claim 1 in which said sleeve is free of side apertures adjacent to said one end.

9. The electrocautery probe of claim 8 in which said one end of the probe is blunt so as to be essentially incapable of penetrating tissue without electrocautery action and said wire is free of insulation adjacent to said one end apart from any insulation provided by said sleeve, and said wire adjacent to said one end fitting loosely in said sleeve.

10. The probe of claim 9 in which at least a portion of said wire remote from said electrode is surrounded by a tubular insulating layer, said insulating layer being slidably removable from the sleeve along with said wire.

11. The probe of claim 10 in which said flexible sleeve fully encloses said thick wire portion, said thick wire portion comprising the wire adjacent to the one end which fits loosely in the sleeve, said flexible sleeve also extending proximally from said thick wire portion along said thin wire portion, said thin wire portion comprising the portion having said insulating layer.

12. An electrocautery probe for penetrating through tissue, which comprises:

a tissue-compatible, flexible sleeve; an exposed electrode carried at and immovably connected to one end of said sleeve, said sleeve being free of side apertures adjacent to said electrode, a wire connected at one end to said electrode, said wire having a distal, relatively thick wire portion adjacent said electrode, said thick wire portion being of a thickness to be manually bendable while tending to retain a shape to which it is bent; said wire also having a proximal, relatively thin wire portion having more flexibility than said thick wire portion, said wire portions being electrically connected together, and an electrical connector attached to an end of said wire opposed to said one end, said connector being suitable for attachment to a source of electrocautery power, said thin wire portion being separate from said sleeve to be removable by pulling from said sleeve when said electrode is cut away or otherwise removed, whereby said probe can penetrate tissue by electrocautery action to form a tissue tunnel, and said electrode and wire can be removed from the sleeve, leaving the sleeve in the tissue tunnel to serve as a drainage catheter, said electrode having a blunt outer end so as to be incapable of penetrating tissue without electrocautery action.

13. The probe of claim 12 in which at least said thin wire portion is covered with an insulating layer that is removable from said sleeve with said wire.

14. The electrocautery probe of claim 12 in which said wire is free of insulation adjacent to said one end apart from any insulation provided by said sleeve, and said wire adjacent to said one end fits loosely in said sleeve.

15. An electrocautery probe for penetrating through tissue, which comprises:

a tissue-compatible, flexible sleeve; an exposed electrode carried at one sleeve and immovably connected to said sleeve, said sleeve being free of side apertures adjacent to said one sleeve; a wire connected at one wire end to said electrode and extending through said sleeve, and an electrical connector attached to an end of said wire opposed to said one wire end, said connector being suitable for attachment to a source of electrocautery power, said wire being substantially separate from said sleeve to be removable by pulling from said sleeve when said electrode is cut away or otherwise removed from the sleeve, said wire being free of insulation adjacent to said one wire and apart from the insulation provided by said sleeve, and said wire adjacent to said one end fitting loosely in said sleeve, whereby said probe can penetrate tissue by electrocautery action to form a tissue tunnel, and said electrode and wire can then be removed, leaving the sleeve and the tissue tunnel to serve as a drainage catheter, one end of said probe being blunt so as to be essentially incapable of penetrating tissue without electrocautery action, said wire comprising a distal, relatively thick wire portion adjacent said electrode, said thick wire portion being of a thickness to be manually bendable and tending to retain a shape to which it is bent; and a proximal, relatively thin wire portion having more flexibility than said thick wire portion, said wire portions being electrically connected together.

16. The probe of claim 12 in which said flexible sleeve fully encloses said thick wire portion and extends proximally from said thick wire portion along said thin wire portion.

17. The probe of claim 16 in which thin wire portion has an insulation layer, while said thick wire portion is free of added insulation, above and beyond said sleeve.

* * * * *

UNITED STATES PATENT AND TRADEMARK OFFICE
CERTIFICATE OF CORRECTION

PATENT NO. : 6,156,035
DATED : December 5, 2000
INVENTOR(S) : Songer, Matthew J.

Page 1 of 1

It is certified that error appears in the above-identified patent and that said Letters Patent is hereby corrected as shown below:

<u>Column 6,</u>
Line 41, "claim 12" should be -- claim 15 --.

Signed and Sealed this

Eighteenth Day of September, 2001

Attest:

*Nicholas P. Godici*

NICHOLAS P. GODICI
*Attesting Officer*  *Acting Director of the United States Patent and Trademark Office*